United States Patent
Weisser et al.

(10) Patent No.: US 6,572,887 B2
(45) Date of Patent: Jun. 3, 2003

(54) POLYSACCHARIDE MATERIAL FOR DIRECT COMPRESSION

(75) Inventors: Eric M. Weisser, Somerset, NJ (US); Judith K. Whaley, Belle Mead, NJ (US); Amos E. Enabosi, Piscataway, NJ (US); Himanshu Shah, Branchburg, NJ (US); Pankaj Rege, Monmouth Junction, NJ (US)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 90 days.

(21) Appl. No.: 09/804,666

(22) Filed: Mar. 12, 2001

(65) Prior Publication Data

US 2002/0054905 A1 May 9, 2002

Related U.S. Application Data

(60) Provisional application No. 60/233,210, filed on Sep. 15, 2000, and provisional application No. 60/200,858, filed on May 1, 2000.

(51) Int. Cl.⁷ .............................. A61K 9/14; A61K 9/20
(52) U.S. Cl. ................... 424/464; 424/465; 424/489; 514/777; 514/778
(58) Field of Search .................. 424/464, 465, 424/489

(56) References Cited

U.S. PATENT DOCUMENTS

| | | | |
|---|---|---|---|
| 3,490,742 A | 1/1970 | Nichols et al. | 251/99 |
| 3,622,677 A | 11/1971 | Short | 424/361 |
| 4,232,052 A | 11/1980 | Nappen | 426/601 |
| 4,383,111 A | 5/1983 | Takeo et al. | 536/102 |
| 4,384,005 A | 5/1983 | McSweeney | 426/250 |
| 4,551,177 A | 11/1985 | Trubiano et al. | 106/210 |
| 5,135,757 A | 8/1992 | Baichwal et al. | 424/465 |
| 5,468,286 A | 11/1995 | Wai-Chiu et al. | 106/210 |
| 5,939,091 A | 8/1999 | Eoga et al. | 424/441 |
| 6,130,321 A | * 10/2000 | Johnson et al. | 536/20 |

FOREIGN PATENT DOCUMENTS

| | | |
|---|---|---|
| EP | 0 659 403 | 11/1994 |
| WO | 00/19982 | 4/2000 |

* cited by examiner

*Primary Examiner*—James M. Spear
(74) *Attorney, Agent, or Firm*—Karen G. Kaiser

(57) ABSTRACT

This invention relates to a method of using compressible polysaccharides having a tap density of less than 0.4 g/ml as a filler/binder for tablets prepared by direct compression, excipient blends including said polysaccharides, a method of tableting an active ingredient therein from the excipient blends and the tablets produced therefrom. More particularly, this invention relates to the use of low-density starches as binders for tablets prepared by direct compression, excipient blends, and methods of tableting an active ingredient therein from such starches. Further, this invention describes a starch-based excipient composition having a tap density of less than 0.4 g/ml, which has excellent moisture resistance.

22 Claims, 4 Drawing Sheets

POLYSACCHARIDE MATERIAL FOR DIRECT COMPRESSION

This application is a regular application based on the priority of provisional applications, U.S. Ser. Nos. 60/233,210 and 60/200,858, filed Sep. 15, 2000 and May 1, 2000, respectively.

FIELD OF THE INVENTION

This invention relates to a method of using compressible polysaccharides having a tap density of less than 0.4 g/ml as a filler/binder for tablets prepared by direct compression, excipient blends including said polysaccharides, a method of tableting an active ingredient therein from the excipient blends and the tablets produced therefrom. More particularly, this invention relates to the use of low-density starches as binders for tablets prepared by direct compression, excipient blends, and methods of tableting an active ingredient therein from such starches. Further, this invention describes a starch-based excipient composition having a tap density of less than 0.4 g/ml, which has excellent moisture resistance.

BACKGROUND OF THE INVENTION

Direct compression is a process by which a powder blend of an active ingredient, such as a drug, and a suitable excipient and/or filler, which is capable of flowing uniformly into a die cavity, are compressed directly into an acceptable tablet. The advantages of direct compression include limiting exposure of the active material to moisture and/or heat, and long-term physical and chemical stability. Direct compression requires only two steps, mixing the dry ingredients and compressing the mixture into a tablet, and hence it is the most preferred and economical method of tableting.

The direct compression process has a number of limitations dependent upon the compactibility, particle size, crystallinity, polymorphism, flowability and density of the excipient as well as the active ingredient. In particular, tablets containing a high dose of an active ingredient which has poor compactibility ordinarily cannot be prepared by direct compression because filler/binders have a limited dilution potential. Thus, one of the most important properties of a filler/binder is high compactability which ensures that the compacted mass will remain bonded after the release of the compaction pressure.

It is common to use a combination of two or more filler/binders in order to obtain a mixture with adequate compactibility, stability, and cost. Only a few excipients can be compressed directly into tablets without physical modification.

Typical direct compression excipients or filler/binders include microcrystalline cellulose, specialty compressible sugars, modified calcium salts, lactose, starches, and dextrose. Of these, microcrystalline cellulose ("MCC") is often the binder of choice. However, MCC has inherent flow problems and is very expensive. Other fillers/binders include physically modified calcium phosphate (di- or tribasic) and specialty compressible sugars, but each filler/binder has its limitations. The calcium salts do not allow for the preparation of tablets with a high level of active ingredient, tend to undesirably alter behavior during prolonged storage and generally require the use of disintegrants. The use of sugars (usually sucrose) present a darkening problem, tend to change tablet crushability with age, and have chemical incompatibility with some drugs. Lactose has limited binding properties and undesirably darkens in the presence of amino substituted drugs. Specialty mannitol and sorbitol compounds have properties similar to sugars, but have limited application, and are used primarily to provide chewable tablets.

Starches and their derivatives have been used as excipients in drug products functioning as disintegrants, diluents and binders. Bolhuis, Gerard K. and Chowhan, Zak T., "Materials for Direct Compression" in *Pharmaceutical Powder Compaction Technology,* Alderborn, 9 & Nystrom Editors, Vol. 71, Chapter 14, 419–500, Marcer Decker, N.Y. In particular, U.S. Pat. Nos. 3,622,677 and 4,072,535 issued to R. W. Short et al. Report that physically modified, partially gelatinized, and pregelatinized starches are useful as binder-disintegrants for direct compression tableting. The modification, which is carried out by passing the starch through closely spaced steel rollers with or without the use of supplemental thermal energy, disrupts and fractures at least some of the granules and results in a mixture of birefringent and non-birefringent granules and fragments, as well as completely solubilized starch (typically about 10–20%). The compacted mass is ground and classified into desired particle size fractions. The resulting starch has limited direct compression binding ability, and the use of an auxiliary binder is often required.

U.S. Pat. No. 4,384,005 issued May 17, 1983 to D. R. McSweeney et al., describes the use of certain hydrolyzed starches as "melting point elevators" in a hybrid wet granulation-direct compression tableting process for preparing nonfriable, rapidly water-dispersable tablets for sweetened or unsweetened beverage tablets. The inclusion of a melting point elevator raises the melting point of the mixture so that the tablets made therefrom do not soften, melt or form a hard core during drying and compression.

Solubilized fractionated starches described in U.S. Pat. No. 3,490,742 issued Jan. 20, 1970 to G. K. Nichols, such as non-granular amylose, are also reportedly useful as binder-disintegrants in direct compression tableting processes. The amylose fraction is non-granular because the starch from which it is derived is totally solubilized in order to free the amylose. This material is prepared by gelatinizing the starch. Then high molecular weight (long chain) amylose is fractioned from the gelatinized starch in water at elevated temperatures. In order to function as a binder, such a starch must contain at least 50% of the native (e.g., long chain) amylose which was present in the starch.

U.S. Pat. No. 4,551,177 issued Nov. 5, 1985 to Trubiano, et al. discloses a compressible starch, useful as a binder for tablets prepared by direct compression. This starch consists of a free-flowing compressible powder derived from a cold-water-insoluble, granular starch. The granular starch is prepared by treatment with an acid, alkali, and/or alpha-amylase enzyme at a temperature below the gelatinization temperature which results in weakened granules having less dense interiors and disrupted surfaces. Likewise, U.S. Pat. No. 5,468,286 issued Nov. 21, 1995 to C. W. Chiu et al. describes enzymatically debranched starches which are also useful as direct compression binders. Both products are substantially crystalline, have relatively high densities and have low dilution potential compared to other binders used in the industry.

Low-density polymers, including polysaccharides, are known to be useful in the preparation of cosmetic or pharmaceutical compositions. Such compositions are disclosed in European Patent App. No. 659,403 wherein a low-bulk density polysaccharide is used as a carrier for an adsorbed oil or oil soluble substance. In addition, U.S. Pat.

No. 4,232,052 issued Nov. 4, 1980 to B. H. Nappen describes a combination of a low-bulk density starch and a grinding agent which forms a carrier suitable for adsorbing high fat foodstuffs. These carriers may be incorporated as adjuvants in processed foodstuffs, tablets, or powders.

Unlike other starches used in direct compression binding, it has been discovered that the low-density polysaccharides of the present invention have unexpectedly excellent compaction properties resulting in tablet crushing strengths comparable to or better than binders currently preferred in the pharmaceutical industry. Thus, the low-density polysaccharides of the current invention advantageously provide binder/filler utility as tablet excipients in direct compression applications.

DETAILED DESCRIPTION OF THE INVENTION

Figure 1:
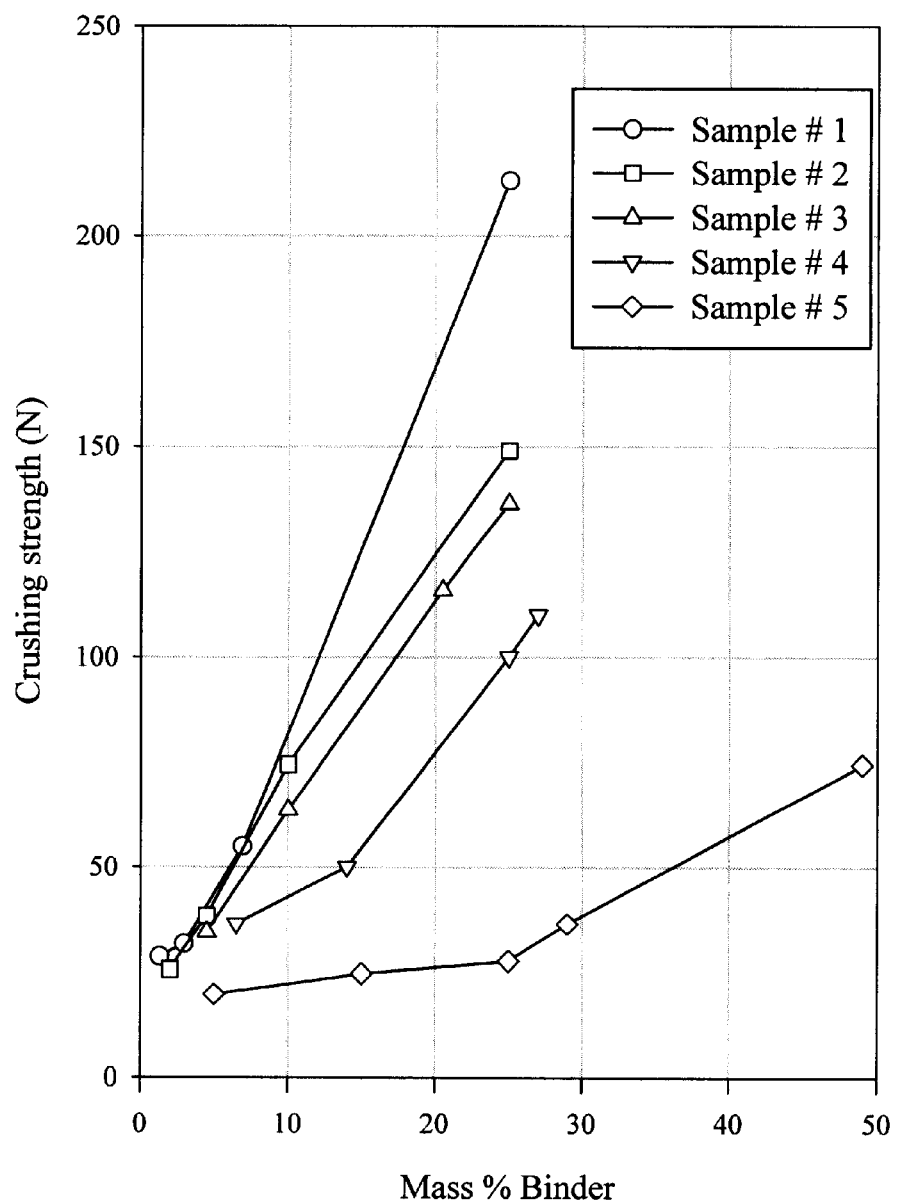
FIG. 1 illustrates that the crushing strength of tablets composed of 25% low-density starch and 75% Dibasic Calcium Phosphate ("DCP") increases as the density of the starch used to prepare the tablets decreases.

This invention relates to a method of using compressible polysaccharides having a tap density of less than 0.4 g/ml as a filler/binder for tablets prepared by direct compression, excipient blends including said polysaccharides, a method of tableting an active ingredient therein from the excipient blends and the tablets produced therefrom. More particularly, this invention relates to the use of low-density starches as binders for tablets prepared by direct compression, excipient blends, and methods of tableting an active ingredient therein from such starches. Further, this invention describes a starch-based excipient composition having a tap density of less than 0.4 g/ml, which has excellent moisture resistance.

The base material for the polysaccharides of this invention can be derived from starches, including the enzymatic, chemical, or heat degradation products of starch, such as dextrins. Also included as base materials are gums, such as gum arabic, alginates, pectinate, carrageenans and cellulosics. As used herein, the term "polysaccharide" may include more than one base material.

All starches and flours (hereinafter "starch") may be suitable for use as base materials herein and may be derived from any native source. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein. Typical sources for the starches are cereals, tubers, roots, legumes and fruits. The nature source can be corn, pea potato, sweet potato, banana, barley, wheat rice, sago, amaranth, tapioca, arrowroot, canna, sorghum, and waxy or high amylose varieties thereof. As used herein, the term "waxy" is intended to include a starch containing at least about 95% by weight amylopectin and the term "high amylose" is intended to include a starch containing at least about 40% by weight amylose. The preferred starch is corn, waxy corn, high amylose corn, potato, tapioca, rice, wheat, sago, or waxy sorghum starch. The more particularly preferred starch is waxy corn and tapioca dextrin and blends thereof.

Conversion products derived from any of the starches, including fluidity or thin-boiling starches prepared by oxidation, enzyme conversion, acid hydrolysis, heat and or acid dextrinization, thermal and or sheared products may also be useful herein. A particularly preferred starch dextrin is tapioca dextrin.

Chemically modified polysaccharides, particularly starches, are also intended to be included as the base material and include, without limitation, those which have been crosslinked, acetylated and organically esterified, hydroxyethylated and hydroxypropylated, phosphorylated and inorganically esterified, cationic, anionic, nonionic, and zwitterionic, and succinate and substituted succinate derivatives thereof. Such modifications are known in the art (see Modified Starches; Properties and Uses, Ed. Wurzburg, CRC Press, Inc., Florida (1986)). Particularly useful are charged based materials; that is those which are cationic, anionic, or zwitterionic.

Physically modified polysaccharides, such as the thermally-inhibited starches described in the family of patents represented by WO 95/04082, may also be suitable for use herein. Also suitable as base materials are pregelatinized starches which are known in the art and disclosed in U.S. Pat. Nos. 4,465,702, 5,037,929, 5,131,953, and 5,149,799. Conventional procedures for pregelatinizing starch are also known to those skilled in the art and described, for example, in Chapter XXII—"Production and Use of Pregelatinized Starch", *Starch: Chemistry and Technology*, Vol. III—Industrial Aspects, R. L. Whistler and E. F. Paschall, Editors, Academic Press, New York, 1967.

Methods for producing low-density starches are known in the art. The methods disclosed herein are examples only, and are not intended to be exclusive means of preparing the low-density starches of the present invention. A first method for preparing a low-density polysaccharide is described in U.S. Pat. No. 4,232,052, which is incorporated herein by reference. The polysaccharides of this invention may be prepared by solubilizing the base material in a solvent, adding a blowing agent and drying the solution.

Solubilizing the base material may be achieved by thermally cooking a slurry of the base material in a solvent, preferably water, and cooling the resultant dispersion to ambient room temperature. Thermal cooking may be achieved either by heating the slurry at elevated temperatures for about 30 minutes while agitating, or by subjecting the slurry to a continuous, direct steam injection cooking apparatus.

The blowing agent may be added to the dispersion prior to drying in order to decrease the tap (and bulk) density of the resultant powders. Tap and bulk density are defined herein, infra. The decrease in density may be accomplished by the expansion of the blowing agent within the spray-dried particle. Any blowing agent may be used which is compatible with the dispersion components (i.e. polysaccharide and water) and capable of expanding the resultant spray dried particle. Particularly suitable blowing agents include, with limitation, carbon dioxide, ammonium salts, and inorganic salts such as carbonates and bicarbonates, more particularly carbonates and bicarbonates such as ammonium carbonate, ammonium bicarbonate, sodium carbonate and sodium bicarbonate.

The blowing agent may be added in any amount desired, dependent upon the blowing agent, the polysaccharide used and the particle tap density desired. In general, the blowing agent will be used in an amount of from about 1 to about 100%, particularly from about 2 to about 70%, more particularly from about 2 to about 50%, by weight of the starch.

Other drying parameters may include, but are not limited to alteration of nozzle size and configuration of the spray drying apparatus, variation of air, steam or fluid pressure, variation of feed rate, amount of starch solids, inlet temperature and vacuum pressure.

The resulting dried material will be in the form of particles containing an open hollow cavity as disclosed by electron beam magnification. The density and particle size will be dependent on the polysaccharide used, solids content of the starting solution, blowing agent concentration and the particular drying method used. Tap densities in the range of between about 0.05 to about 0.4 g/ml can be obtained depending upon the solids concentration of the solubilized base, blowing agent and drying parameters. Tap densities of less than about 0.05 g/ml can be obtained by using a low solids solubilized base solution and a high concentration of blowing agent.

A second method of preparing the low-density starches of this invention involves allowing a dispersed starch to precipitate in dehydrating media. This may be achieved by thermally cooking a slurry of the base starch having a solids content of from about 10% to about 35% and cooling the dispersion to ambient room temperature. Thermal cooking can be achieved either by heating the slurry to temperatures of above the gelatinization temperature of the starch for about 30 minutes while agitating, or by subjecting the slurry to a continuous, direct steam injection cooking apparatus.

The resultant dispersed starch is then introduced into a dehydrating medium with mechanical agitation. The starch precipitates, is filtered out of solution, washed with additional dehydrating medium and dried. The preferred dehydrating medium is an alcohol, particularly methanol. Filtration may be accomplished under vacuum, and drying may be accomplished via a variety of techniques known in the art including air drying, spray drying or drying in a dessicator. Optionally, the resultant starch solid may be further dried in a forced draft. In addition, the starch solid may optionally be sieved, or further ground to achieve the desired particle size. Starches produced via this technique have a tap density of below about 0.4 g/ml.

A third method of preparing the low-density starches of this invention may be achieved by introducing the dispersed starch produced by the second method with shear into a saturated aqueous solution of a salt, such as magnesium sulfate. The rate of the addition of the dispersed starch is adjusted so that the jacketed temperature of the addition mixture is maintained between about −5° C. to about 85° C. and particularly between about −5° C. to about 40° C. The resultant starch precipitate is then filtered out of solution, dried and prepared as described for the second method discussed above. A particularly preferred drying step for the third method is freeze-drying. The third method of preparing low-density starches is especially suitable for starches containing amylose, particularly those starches with an amylose content of above about 15%, more particularly above about 50% and most particularly above about 65%.

A tap density of 0.4 g/ml correlates to a porosity of 0.70 for the low-density starches of this invention. Tap density can be correlated to porosity for a given base material for the purpose of estimating the suitability of such an excipient for binding. However, when comparing the porosity of different bases via their tap density, the neat density of the materials must be taken into account. The porosity of such a processed powder bed, $\epsilon$, is related to the tap density, $\rho_{tap}$, of the binder and the neat density of the base material, $\rho_{neat}$, according to equation (1) below, $$\varepsilon = \left[1 - \left(\frac{\rho_{tap}}{\rho_{neat}}\right)\right]. \qquad (1)$$

Tap and neat densities, as used herein, are defined herein, infra. The low-density starches used as illustrations of this invention all have neat densities of approximately 1.1 to 1.3 g/ml. A tap density of about 0.4 g/ml is thus equivalent to a porosity of about 0.70. Though the density of the polysaccharides of this invention are described primarily as tap densities, one of ordinary skill in the art understands that polysaccharides having a porosity of greater than about 0.70 are also included in the description of this invention.

Although any polysaccharide with a tap density less than about 0.4 g/ml is suitable in the invention, polysaccharides with tap densities of less than about 0.2 g/ml are particularly suitable and less than about 0.05 g/ml are more particularly suitable. The correlation of low-density starches with the increased crushing strength of tablets made from these starches via direct compression is illustrated in FIG. 1. For example, a starch having a tap density of 0.030 g/ml exhibited a crushing strength of about 213 Newtons ("N") in a tablet containing 25% binding vehicle and 75% dibasic calcium phosphate (DCP), whereas a crushing strength of only 27.5 N was demonstrated for a starch having a tap density of 0.440 g/ml. A tablet made from 100% DCP has a crushing strength of 19.6 N.

The moisture content of hydrophilic binders is known to affect binding efficiency at low moisture levels. Prior art compositions, when formulated into tablets, have shown an unacceptable loss in crushing strength when exposed to high moisture conditions. Surprisingly, the tablets prepared from the low-density starches of the present invention, did not show the same loss in crushing strength when exposed to the same moisture conditions. This is particularly true of high molecular weight polysaccharides. A tablet prepared according to this invention will show less than 30%, and more particularly less than 20% loss in crushing strength when exposed to 95% relative humidity ("RH") at 25° C. for 3 hours.

Figure 2:
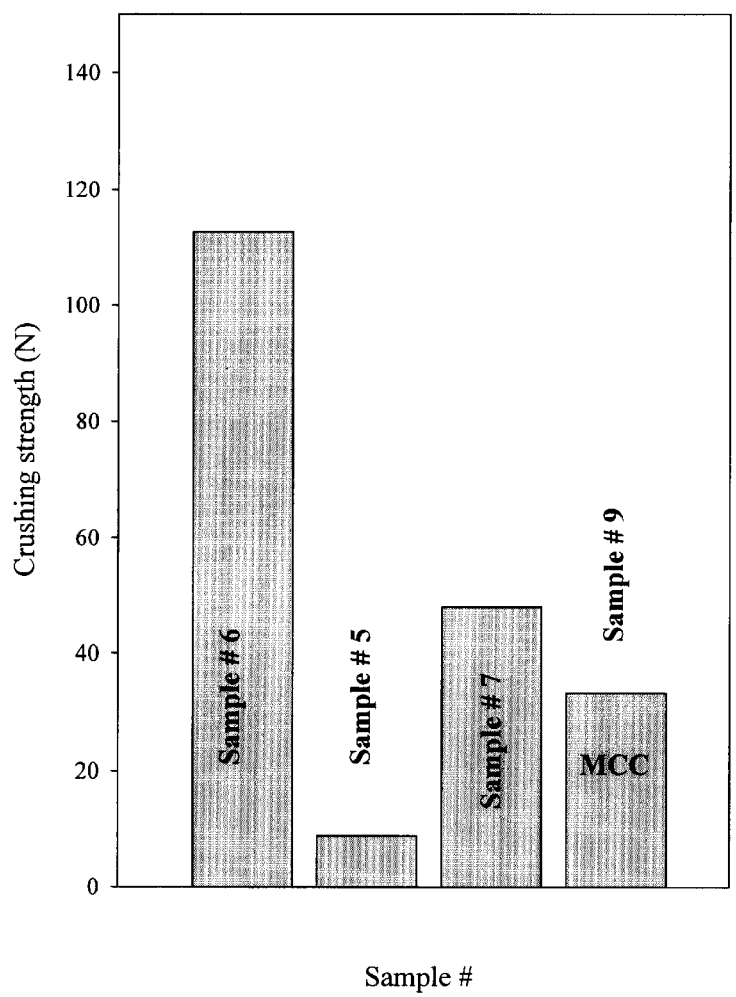
FIG. 2 illustrates that tablets prepared from the low-density starches of this invention as a 20% binder for a poorly compressible active ingredient (ascorbic acid) exceed or are equal to the crushing strength of a tablet using 20% MCC as the binder.

The low-density starches of this invention also demonstrate excellent binding properties as compared to commercial binders used for direct compression, such as MCC. For example, FIG. 2 illustrates that tablets formulated with the low-density starches of this invention as a 20% binder exceed or are equal to the crushing strength of a tablet prepared using MCC as a 20% binder.

The low-density polysaccharides of this invention may also be used in conjunction with at least one other excipient in order to manipulate formulation and tablet properties. Additional excipients are often starch powders, which have minimal binding functionality. Typical starch powders used as excipients include pregelatinized starches, such as Starch 1500® (Colorcon), NATIONAL 78-1551 (National Starch & Chemical Company), or corn starch NF (e.g. PURITY® 21 starch—National Starch & Chemical Company). An effective amount of additional excipient is defined to be the amount of excipient required to confer optimum properties upon the tablet. Optimum tablet properties may include, but are not limited to, the desirable degree of tablet crushability, friability, disintegration, dissolution and bioavailability.

When necessary, disintegrants may be used. Said optional disintegrants include, without limit, native starches, modified starches, gums, cellulose derivatives, microcrystalline cellulose, clays, effervescent mixtures and enzymes. The amount of binder (or excipient blend), active ingredient, and lubricant, disintegrant and/or diluent, if any, will depend not only on potency desired but also on the compatibility of the components and the tablet crushability, friability, disintegrability, dissolution, and/or stability of the final tablet. Anti-adherents, glidants, flavors, coloring agents and the like may also be used. Given the minimum and preferred characteristics desired in the final product, the tolerable limits on the weight ratio of the components may be easily determined by the skilled practitioner.

The active ingredients which may be employed herein constitute all active ingredients and include pharmacologically active ingredients, including poorly compressible active ingredients such as, for example, ascorbic acid and ibuprofen. The particular nature of the active ingredient is not critical, however, and also includes non-pharmaceutical active ingredients such as pulverized detergents, dyes, pesticides and food ingredients, including nutritional supplements.

EXAMPLES

The following methods and procedures were used to prepare the starches and blends thereof, and include the preparation and evaluation of tablets containing the compressible starches of this invention. The methods and procedures are referred to throughout the Examples contained herein.

Methods & Procedures
Measurement of Density

Bulk Density: A known mass of a starch sample was introduced into a graduated 50 ml cylinder, and the volume of the sample determined to the nearest millimeter. The bulk (or poured) density was then obtained by dividing the mass of the solid by the unsettled apparent volume.

Tap Density: The tap density was then obtained by taking the graduated cylinder containing the known mass of powder used to determine the bulk density and placing it in a Erweka SVM 22 Tap Volumeter, or similar apparatus, set for 500 strokes. After tapping was completed, the resulting volume of the material is recorded. The tap density was then determined as the weight of the material in the graduated cylinder divided by the volume of material after tapping is completed.

Neat Density: Neat density was determined by taking a known mass of starch sample and grinding it to remove any large scale porosity or structure from the sample. The ground starch was then placed in a 50 ml volumetric flask and ethanol added to a total volume of 50 ml. The volume and density of the starch is calculated from the volume, weight and density of the ethanol added to the flask.

Blend Preparation

The starches were mixed with the excipient, then mixed in a Turbula (WAB, Type T2F) mixer for 5 minutes. The mixture is sieved through a 420-micron sieve and the fraction passing through the screen is used. After mixing, the powders are stored in airtight containers until they are used.

Tableting Procedures
Procedure 1—Piccola 10-station Tablet Press

The blends were compressed using an instrumented Piccola 10-station tablet press. One station on the tablet press was fitted with a 12.5 millimeter flat-faced punch and corresponding die. The tablet weights were adjusted to 500 mg and the tablets compressed at 13.9 Mega Pascals ("MPa") compression force.

Procedure 2—Single Punch Tablet Press (Globepharma Model MTCM-1)

The single station tablet press was fitted with a 12.5 mm punch and a corresponding die. 500 mg of the powder was weighed (1% accuracy) fed into the die cavity and compressed at 13.9 MPa compression force. The compaction time took about two to three seconds.

Crushing Strength Measurements

Crushing strengths were determined for five tablets, prepared according to either Procedure 1 or 2, using a Pharmatron (Model 6D) tablet tester.

EXAMPLES

The following examples will illustrate the embodiments of this invention. Sample numbers are assigned to materials used as binders/fillers and represent the binders of the present invention and other commercially known fillers/binder. Tablets formulated from a certain binder/filler are assigned a particular Sample number corresponding to the particular binder/filler comprised therein, but do not necessarily correspond to the same tablet formulation. The same Sample number is used to describe the same binder/filler throughout the examples. If not specified otherwise, all percents are weight percents.

Example 1

Use of a Low-density Starch as a Direct Compression Binder and Preparation Thereof Via Using a Latent Gas (Method One)

The use of the low-density starches of the present invention as direct compression binders was evaluated by making 100% low-density starch tablets and determining their tablet crushing strengths.

Low-density waxy corn starch (Sample 1) was prepared by jet cooking a 17.86% by weight slurry of waxy corn starch at 165° C., cooling the mixture to 60° C. and adjusting the solids to 8% by weight. This was followed by the addition of 50% ammonium carbonate on weight of starch. The resultant solution was then spray dried in a Niro spray drier with an inlet temperature set at 320° C. using a conventional ¼ J nozzle with air atomization at 620 kPa. The collected starch had a tap density of 0.030 g/ml (Sample 1).

The low-density starch thus prepared was evaluated as a direct compression binder at 100% of tablet formulation by comparison with other commercially available filler/binders including Starch 1500® (Colorcon, Lot 8090171), Microcrystalline Cellulose, (Avicel® PH-102 NF, FMC Lot #2813) and dibasic calcium phosphate (Spectrum, Lot OS0311), Tablets composed of 100% of each binder were prepared according to Procedure 1and their crushing strength was measured. The data is reported in Table 1.

TABLE 1

| Description of binder/filler | Average Crushing Strength (N) | Tapped Density (g/ml) |
|---|---|---|
| Sample 1 | >453.1* | 0.030 |
| Partially pregelatinized starch | 31.4 | 0.740 |
| Microcrystalline cellulose (MCC) | 341.3 | — |
| 100% Dibasic calcium phosphate (DCP) | 19.6 | — |

*Machine limit is 453 N.

The data demonstrated that the low-density starch of the present invention provided tablets with a higher crushing strength than other commercially available binders, when used at 100%. In particular, the tablets of this invention had significantly higher crushing strength than tablets prepared from other starch-based filler/binders such as tablet prepared from Starch 1500®. In addition, the crushing strength of the tablets of this invention were superior to that of conventional commercially available binders such as MCC or DCP.

Example 2

Use of a Low-density Amorphous Starch as a Direct Compression Binder in Presence of Other Excipients The low-density starches of the present invention were blended with three common excipients used in the pharmaceutical industry in direct compression applications to demonstrate that their binding ability is independent of excipient.

The low-density waxy corn starch prepared according to Example 1 (Sample 1) was blended with lactose anhydrous (Quest, Lot MRP 833555), dibasic calcium phosphate, (Spectrum, Lot OS0311), and Starch 1500®, (Colorcon, Lot 8090171) to afford 5% w/w starch powder blends. Tablets were prepared from each powder blend according to Procedure 1. The crushing strength data for the three excipient blends as well as the crushing strength of placebo tablets prepared from the excipient alone are reported in Table 2.

TABLE 2

| Excipient | Mass Fraction (w/w) Sample 1 (tap density = 0.030 g/ml) | Crushing Strength (N) |
|---|---|---|
| Dibasic calcium phosphate | 0.00 | — |
|  | 5.01 | 42.2 |
| Lactose Anhydrous | 0.00 | 55.9 |
|  | 5.01 | 82.4 |
| Starch 1500 ® | 0.00 | 11.8 |
|  | 5.00 | 28.4 |

As the data in Table 2 illustrates, the crushing strength of the tablets was significantly enhanced by the 5% w/w inclusion of the low-density starch (Sample 1) demonstrating the potential of low-density starches to operate as effective binders in excipient blends for direct compression applications.

Example 3

Effect of Density on the Crushing Strength of Placebo Tablets

This example illustrates how the crushing strength of a tablet may be increased by lowering the density of the low-density starch which is being used in an excipient blend. This example also illustrates that tablet crushing strength is independent of the type of starch base used to produce the low-density starch.

Four low-density waxy corn starches were prepared using the method described in Example 1, with 50% ammonium carbonate on weight of starch (Sample 1), 37.5% (Sample 2), 25% (Sample 3) and 12.5% (Sample 4) to provide low-density starches with a range of densities. For comparison purposes, a low-density starch also prepared from a drum dried waxy corn starch (Sample 5) with a tap density greater than 0.4 g/ml and tapioca dextrin (Sample 6, preparation of the starch based described in U.S. Pat. No. 4,232,052). Finally, a low-density starch blend was prepared from a 50:50 w/w mixture of Sample 5 and Sample 6 (Sample 7).

These low-density starches were then sieved on a Tyler Rotap Sieve Shaker for 10 minutes to collect the fraction having a 75–250 micrometer particle size. A 25% blend of the above materials were made with dibasic calcium phosphate (Spectrum, Lot OS0311), tabletted according to Procedure 2 and evaluated for crushing strength. The data is presented in Table 3.

TABLE 3

| Sample # | Mass Fraction Of Sample | Average Crushing Strength (N) | TAP Density (g/ml) |
|---|---|---|---|
| Sample 10 | * | 19.6 | — |
| Sample 1 | 25.00% | 212.8 | 0.030 |
| Sample 2 | 25.00% | 149.1 | 0.045 |
| Sample 3 | 25.00% | 136.3 | 0.106 |
| Sample 4 | 25.00% | 100.0 | 0.155 |
| Sample 5 | 25.00% | 27.5 | 0.440 |
| Sample 6 | 25.00% | 174.6 | 0.103 |
| Sample 7 | 25.00% | 78.5 | 0.20 |

*Tablet is 100% DCP

As is demonstrated in Table 3, the lower the tap density of the starch used in the blends, the higher the crushing strength of the corresponding tablet. The starch (Sample 5) with a tap density above 0.4 g/ml did not perform as well as any of the lower density starches or excipient blends containing low-density starches. In addition, tablets prepared from low-density tapioca dextrin had a similar crushing strength to the waxy corn low-density starch of similar tap density. Accordingly, the crushing strength of a tablet formulated from the above materials was independent of the type of material used. In conclusion, the tap density of the starches, or blend of starches, was the critical factor which conferred crushing strength upon tablets prepared therefrom.

Example 4

Effect of the Density of the Starch on the Crushing Strength of Placebo Tablets—Comparison With Commercial Excipients This example defines the upper limit of starch tap density which confers optimum crushing strength on tablets prepared from the starch of this invention.

The starches evaluated as tablet binders in Example 3 were included in this Example. In addition, Starch 1500® (Sample 8, Colorcon, Lot 8090171) was evaluated as an example of a commonly used filler/binder starch-based excipient. Microcrystalline cellulose, MCC, (Sample 9, Avicel® PH-102 NF, FMC Lot #2813) was also evaluated as a commonly used direct-compression excipient.

Blends of the above described starches and MCC were made at 25% mass fraction with DCP were tabletted according to Procedure 2 and their crushing strengths measured and reported in Table 4.

TABLE 4

(25% mass fraction binder with DCP)

| Binder Sample # | Average Crushing Strength (N) | Tap Density (g/ml) |
|---|---|---|
| 1 | 212.8 | 0.030 |
| 2 | 149.1 | 0.045 |
| 3 | 136.3 | 0.106 |
| 4 | 100.0 | 0.155 |
| 5 | 27.5 | 0.440 |
| 6 | 174.9 | 0.103 |
| 7 | 78.5 | 0.200 |
| 8 | 17.7 | 0.740 |
| 9 | 54.9 | — |

Tables incorporating the low-density starch blends of the present invention, having tap densities of less than 0.4 g/ml, preferably less than 0.2 g/ml and more preferably below 0.1 g/ml, showed significant improvement in crushing strength as compared to industry standards (i.e. Samples 8 and 9).

Example 5

Dilution Potential of Low-density Starches Used as Direct Compression Excipients—Dilution With Ascorbic Acid This example illustrates that the low-density starches of this invention can be used at a high dilution potential when tabletted with a poorly compressible drug, ascorbic acid (Changzhou Benchi Pharmaceutical Co, Lot 9909014), as compared to other commonly used direct compression binders which have a high dilution potential, such as MCC.

A low-density tapioca dextrin (Sample #6) and a low-density waxy corn starch (Sample #5), and blends thereof (Sample #7), were formulated with ascorbic acid and tabletted according to Procedure 2. Corresponding blends of MCC (Sample #9, Avicel® PH-102 NF, FMC Lot #2813) were also formulated with ascorbic acid and tabletted according to Procedure 2. The crushing strength of the tablets was measured and the data reported in Table 5.

TABLE 5

| Sample %: Ascorbic Acid % | Sample # | Average Crushing Strength (N) | Tap Density (g/ml) |
|---|---|---|---|
| 20%:80% | 6 | 112.8 | 0.103 |
|  | 5 | 8.8 | 0.440 |
|  | 7 | 48.1 | 0.200 |
|  | 9 | 33.3 | — |
| 10%:90% | 6 | 34.3 | 0.103 |
| 0:100% | Could not be compressed at 13.9 MPa | | |

Tablets prepared with 20% binder prepared from the starches or dextrins having a tap density below 0.4 g/ml, and blends thereof, had greater crushing strength than tablets prepared with 20% MCC (w/w %), the most commonly used direct compression binder in the pharmaceutical industry. The lowest density starch used in this study (Sample 6, 0.103 g/ml) produced tablets with more than three times the crushing strength of tablets prepared with the same binder percentage. A tablet prepared with only 10% binder prepared from Sample 6 had comparable crushing strength to a tablet prepared with 20% MCC.

Example 6

The Effect of Density and Concentration of the Low-density Starch on the Crushing Strength of Tablets Containing an Active Principle This example illustrates the effect of the density of the starches of the present invention as well as starch concentration on the crushing strengths of tablets containing an active principle or other commercial excipient.

Ibuprofen (Lot #C699100, H&A industrial Inc, Ontario, Canada) and Starch 1500® were mixed with the low-density starches of the present invention to yield a final composition containing 50% active and either 0, 5, or 10% of the low-density starch. The results are reported in FIG. 1.

Figure 3:
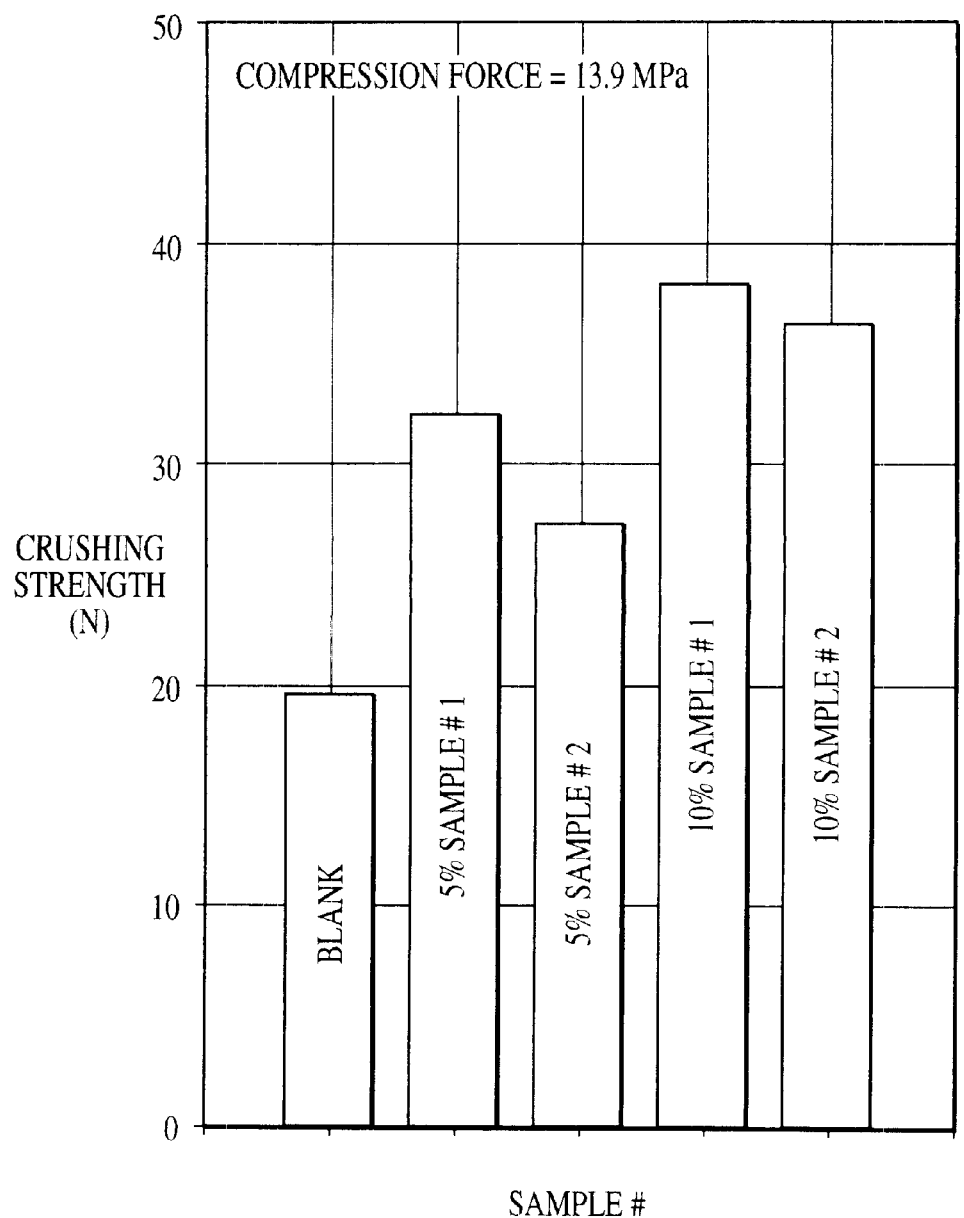
FIG. 3 illustrates that the crushing strength of tablets formulated with 5% of low-density starch form harder tablets that those formulated without such starch.

FIG. 3 shows that the crushing strength of tablets formulated with 5% of the low-density starches form harder tablets than tablets formulated without the low-density starch. Higher percentages of the starches resulted in harder tablets.

Example 7

The Effect of Moisture on the Crushability of Tablets Prepared From Low and High Molecular Weight Low-density Starches This example demonstrates that high molecular weight low-density starches, such as native starches, have superior crushing strength compared to tablets made from lower molecular weight low-density starches, such as dextrins, in high moisture environments.

Tablets containing 25% binder and 75% dibasic calcium phosphate were formulated using Sample 1 and Sample 6. The formulations were compressed using Procedure 2 and their crushing strengths measured. Three tablets of each formulation were placed in an approximately 95% relative humidity environment at 25° C. for 3 hours ("high humidity conditions"). After removal, the crushing strength was determined. The data is tabulated in Table 6.

TABLE 6

| Exposure to 95% RH | Sample # | Average Crushing Strength (N) | Molecular Weight |
|---|---|---|---|
| Before Exposure | 1 | 212.8 | High |
|  | 6 | 174.6 | Low |
|  | 7 | 112.8 | High + Low |
| 3 hours After Exposure | 1 | 193.2 | High |
|  | 6 | 94.1 | Low |
|  | 7 | 106.9 | High + Low |

These results indicate that a tablet made from a high molecular weight material (Sample 1) loses only 9.2% of its crushing strength. A Tablet made from a blend of high and low molecular weight material (Sample 7) loses even less crushing strength, only 5% loss. In contrast, a tablet including only lower molecular weight materials (Sample 6), loses more than 40% of its crushing strength.

Thus, the polysaccharides of this invention, which have a molecular weight higher than tapioca dextrin (Sample 6) and a tap density of less than 0.2 g/ml lose less than 25% of their crushing strength under high humidity conditions.

Example 8

The Effect of Low-density Starch Incorporation on the Compression Force Needed to Make Tablets This example illustrates the functionality of low-density starch as binder in tablet formulations.

The low-density starch was evaluated as a binder in lactose and 50:50 w/w % lactose/MCC blends. The powder blends of Sample 1 and lactose and/or MCC were made containing 0, 1, 3, 5, or 10% wt/wt % of the low-density starch. The force needed to compress the powders into tablets with a crushing strength of 98N (using procedure 2) was measured and recorded.

Figure 4:
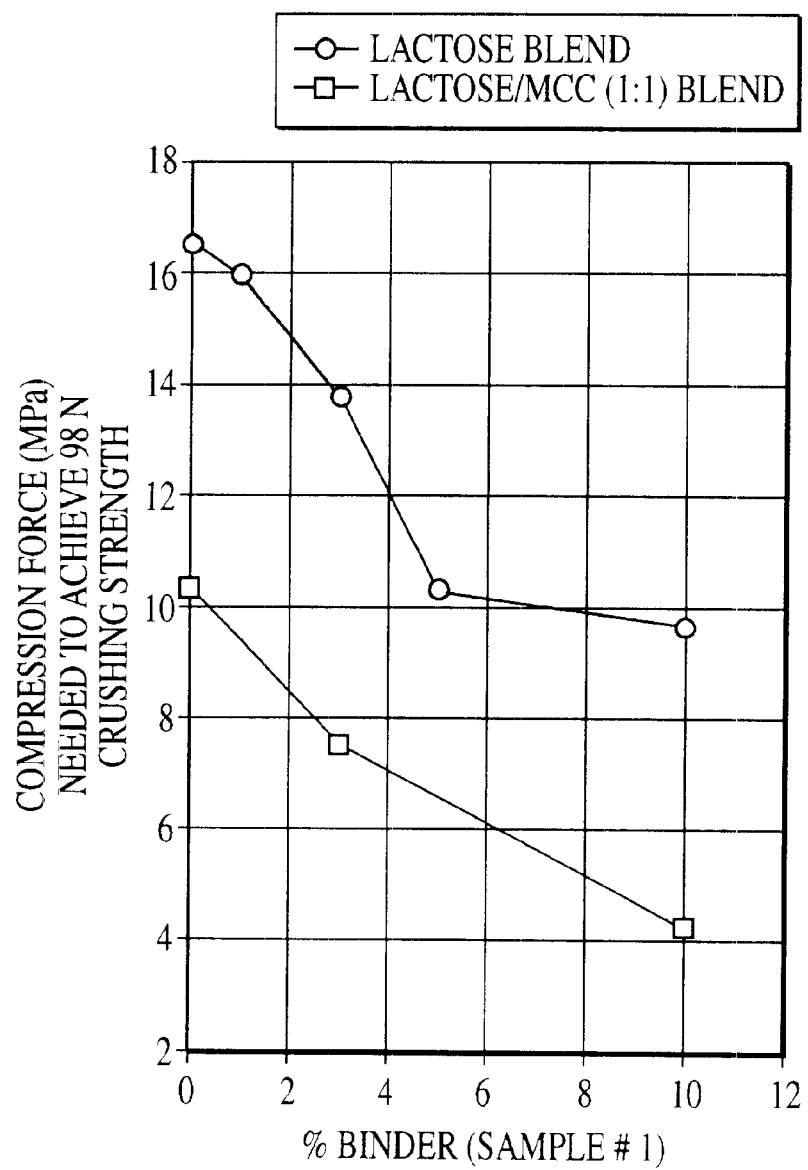
FIG. 4 illustrates that the increase in the mass fraction of the low density starch of the tablet reduces the compression force needed to produce tablets having a crushing strength of 98N.

As illustrated by FIG. 4, an increase in the mass fraction of the low-density starch of the tablet reduced the compression force needed to produce tablets having a crushing strength of 98N. A reduction of the required compression force is indicative of the binding functionality of the low-density starch.

Example 9

The Preparation of Low-density Starch Via Alcohol Precipitation (Method Two)

This example demonstrates that suitable low-density starches may be prepared by precipitation out of a dehydrating media, such as alcohol, thus obviating the need for a gas or latent gas.

The starch was prepared by slurrying a 10% by mass waxy corn starch in water, heating the slurry in a boiling water bath for 30 minutes, and cooling the resultant starch solution to room temperature. The starch was precipitated out by adding the cooled starch solution slowly to methanol to form a 20% by weight aqueous methanol solution (100 parts starch cook to 450 parts methanol). The solution was decanted off the precipitate, an equal volume of fresh solution was added, and the sample allowed to stand overnight. The starch was recovered by filtration, air-dried, ground and passed through a 240 micron sieve. The resultant starch product was determined to have a tap density of 0.300 g/ml.

This low-density starch product was blended with dibasic calcium phosphate (DCP) in a ratio of 25:75 by weight blend (starch:DCP) and tabletted according to Procedure 2. The crushing strength of the tabletted blend was 87 N, significantly higher than a corresponding tablet in which the industry standard MCC was substituted for the low-density starch (crushing strength of only 55 N).

Example 10

The Preparation of Low-density Starch Via Precipitation of the Starch From an Aqueous Salt Solution (Method Three)

This example illustrates a third method for preparing the low-density starches of the present invention comprising precipitating starch out of an aqueous salt solution.

The starch was prepared by slurrying dispersed 10% Hylon® VII starch (National Starch & Chemical Co.) in water and heating the slurry in a boiling water bath for 30 minutes. The hot dispersed starch solution was then added to a saturated aqueous solution of magnesium sulfate with mechanical shear. The rate of the addition was adjusted to maintain the temperature of the jacketed solution to about 30° C. over three hours. The agitation was maintained for three hours.

The starch was then filtered out of solution, washed with water, re-slurried in water and freeze-dried to 5.2% moisture by weight. The resultant starch had a tap density of 0.19 g/ml. The crushing strength of a tablet formulated from 25% starch and 75% DCP which had been tabletted by Procedure 2 had a crushing strength of 92 N, similar to the other low-density starches of the present invention.

We claim:

1. A polysaccharide having a tap density of less than about 0.05 g/ml.

2. The polysaccharide of claim 1, wherein the polysaccharide is at least one starch.

3. The polysaccharide of claim 2 wherein the at least one starch is selected from the group consisting of corn, waxy corn, high amylose corn, potato, tapioca, rice, sago, wheat or waxy sorghum starch.

4. A polysaccharide having a tap density of less than about 0.2 g/ml which, when used in an binding effective amount in a tablet, prevents the crushing strength of the tablet from decreasing more than about a 20% decrease in crushing strength when exposed to 95% relative humidity at 25° C. for 3 hours wherein the crushing strength is measured according to Procedures 1 or 2, herein.

5. The polysaccharide of claim 4, wherein the tap density is less than about 0.1 g/ml.

6. The polysaccharide of claim 4, wherein the polysaccharide is at least one starch.

7. A directly compressible tablet comprising a polysaccharide having a tap density which has been decreased to less than about 0.4 g/ml, and an active agent.

8. The tablet of claim 7, wherein the polysaccharide has a tap density is less than about 0.2 g/ml.

9. The tablet of claim 7, wherein the polysaccharide has a tap density is less than about 0.05 g/ml.

10. The tablet of claim 7, wherein the polysaccharide is at least one starch.

11. The polysaccharide of claim 10 wherein the at least one starch is selected from the group consisting of corn, waxy corn, high amylose corn, potato, tapioca, rice, sago, wheat or waxy sorghum starch.

12. The tablet of claim 7, wherein the at least one starch is a blend of tapioca dextrin and pregelatinized waxy corn.

13. The tablet of claim 7, wherein the tablet is a pharmaceutical tablet.

14. The tablet of claim 7, wherein the active agent is poorly directly compressible.

15. A directly compressible tablet comprising a polysaccharide, an excipient, and an active agent, wherein a mixture of the polysaccharide and the excipient has a tap density of less than about 0.4 g/ml.

16. The tablet of claim 15, wherein the tap density of the mixture is less than about 0.2 g/ml.

17. The tablet of claim 15, wherein the polysaccharide is at least one starch.

18. The tablet of claim 17, wherein at least one starch is a blend of tapioca dextrin and pregelatinized waxy cornstarch.

19. A method of making a tablet comprising directly compressing a polysaccharide having a tap density of less than about 0.4 g/ml and/or a porosity of no more than about 0.7, and an active agent.

20. The method of claim 19, wherein the polysaccharide is a blend of tapioca dextrin and pregelatinized waxy corn.

21. A method of making a tablet comprising directly compressing a polysaccharide, an excipient, and an active agent, wherein a mixture of the polysaccharide and the excipient has a tap density of less than about 0.4 g/ml.

22. The method of claim 21, wherein the polysaccharide is a blend of tapioca dextrin and pregelatinized waxy corn starch.

* * * * *